United States Patent [19]

Henrick et al.

[11] 4,297,297

[45] Oct. 27, 1981

[54] α-CYANO-β-(SUBSTITUTED-ANILINO)-N-ETHOXYCARBONYLACRYLAMIDE INTERMEDIATES

[75] Inventors: Clive A. Henrick; Jeffrey N. Labovitz, both of Palo Alto, Calif.; Roland T. V. Fox, Crowthorne, England; William G. Rathmell, Wokingham, England; Margaret C. Shephard, Maidenhead, England

[73] Assignees: Zoecon Corp., Palo Alto, Calif.; Imperial Chemical Industries Limited, England

[21] Appl. No.: 170,243

[22] Filed: Jul. 18, 1980

Related U.S. Application Data

[60] Division of Ser. No. 23,517, Mar. 23, 1979, Pat. No. 4,266,056, which is a continuation-in-part of Ser. No. 894,307, Apr. 7, 1978, abandoned, which is a continuation-in-part of Ser. No. 892,560, Apr. 3, 1978, abandoned.

[51] Int. Cl.$^3$ ............................................ C07C 121/78
[52] U.S. Cl. ........................ 260/465 D; 260/340.5 R; 260/465.4
[58] Field of Search .................... 260/465 D; 544/311

[56] References Cited

PUBLICATIONS

Atkinson et al., J. Chem. Soc., pp. 4118–4123, (1956).

*Primary Examiner*—Dolph H. Torrence
*Attorney, Agent, or Firm*—Donald W. Erickson; Thomas T. Gordon

[57] ABSTRACT

Novel 1-substituted uracils, synthesis and intermediates therefor, and compositions for the control of pests.

19 Claims, No Drawings

α-CYANO-β-(SUBSTITUTED-ANILINO)-N-ETHOXYCARBONYLACRYLAMIDE INTERMEDIATES

This is a division of Ser. No. 023,517, filed Mar. 23, 1979, U.S. Pat. No. 4,266,056 which is a continuation-in-part of Ser. No. 894,307, filed Apr. 7, 1978, abandoned, which is, in turn, a continuation-in-part of Ser. No. 892,560, filed Apr. 3, 1978, abandoned, the entire disclosures of which are incorporated herein by reference.

This invention relates to novel 1-substituted uracils, synthesis and intermediates therefor, and compositions for the control of pests, especially fungi and bacteria.

The 1-substituted uracils of the present invention are represented by the following formula A:

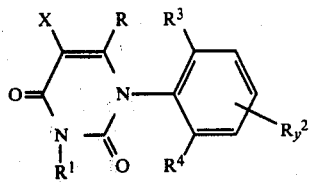

(A)

wherein, each of R and $R^1$ is hydrogen, methyl or ethyl;

$R^2$ is lower alkyl, lower alkoxy, bromo, chloro, fluoro, lower haloalkyl, cyano, nitro, lower alkylthio, hydroxy, lower alkylcarbonyl, lower alkoxycarbonyl, lower haloalkoxy, cycloalkyl, cycloalkalkyl, lower haloalkylthio, lower alkenyl or lower alkynyl;

$R^3$ is hydrogen or independently selected from the values of $R^2$;

$R^4$ is hydrogen or independently selected from the values of $R^2$; and

X is hydrogen, carbamoyl, or cyano; and y is zero, one, two or three.

The synthesis of the compounds of formula A (X is cyano, $R^1$ is hydrogen) can be outlined as follows:

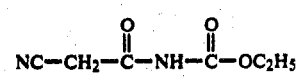

(I)

(II)

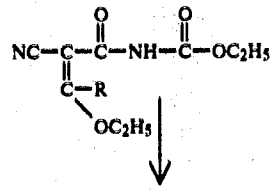

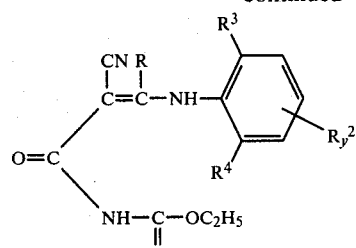

(III)

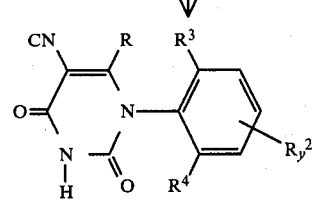

(A')

In the practice of the above synthesis, N-ethoxycarbonylcyanoacetamide (I) is reacted, for example, with triethyl orthoformate in acetic anhydride to prepare α-cyano-β-ethoxy-N-ethoxycarbonylacrylamide (II, R is hydrogen). The use of triethyl orthoacetate and triethyl orthopropionate in place of triethyl orthoformate gives II wherein R is methyl and ethyl, respectively. II, in ethanol, is heated with a substituted aniline (II') to obtain the β-substituted anilino compound III.

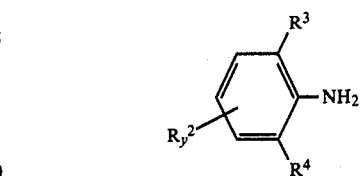

(II')

III is cyclized on heating in a high boiling solvent, preferably a solvent in which III is soluble, such as p-cymene, tetralin, ortho-dichlorobenzene and the like, to yield the 5-cyano-1-substituted phenyl uracil (A'). The compounds of formula A wherein $R^1$ is methyl or ethyl are prepared by alkylation using, for example, dimethyl sulfate. Each step of the above outlined synthesis proceeds in essentially quantitative yield with II, III and A in the form of solids convenient to separate by filtration. The above outlined synthesis follows the synthetic route reported by Senda et al., *Chem. Pharm. Bull.* 20(7), 1380–1388 (1972) and literature cited therein. CF. Lees et al., *J. Chem. Soc.* (C), 1519 (1968); Senda et al., *J. Org. Chem.* 40(3), 353 (1975); and Offenlegungsschrift No. 25 09 037 (1976).

The compounds of the present invention of formula A wherein X represents hydrogen are prepared by heating a 5-cyano compound of formula A or A' with HBr for several hours following the procedure of Senda et al., *Chem. Pharm. Bull.* 22(1), 189–195 (1974) or sulfuric acid following the procedure of Enders et al., Offenlegungsschrift No. 25 09 037 (1976).

The compounds of formula A wherein X represents carbamoyl (—$CONH_2$) are prepared according to the procedure of Enders et al., supra, by treatment with 48% HBr or according to the procedure of Atkinson et al., *J. Chem. Soc.*, 4118–4123 (1956) using alkaline hydrolysis.

The term "lower alkyl," as used herein, refers to a lower alkyl group of one to six carbon atoms. The term "lower alkoxy," as used herein, refers to a lower alkoxy group of one to six carbon atoms. The term "lower alkylthio," as used herein, refers to a lower alkylthio group of one to six carbon atoms. The term "lower haloalkyl," as used herein, refers to a lower alkyl group substituted with one to three atoms of bromine, chlorine or fluorine. The term "lower haloalkoxy," as used herein, refers to a lower alkoxy group substituted with one to three atoms of bromine, chlorine or fluorine. The term "lower alkylcarbonyl," as used herein, refers to a lower alkylcarbonyl group of two to seven carbon atoms. The term "cycloalkyl," as used herein, refers to a cycloalkyl group of three or four carbon atoms. The term "cycloalkalkyl," as used herein, refers to a cycloalkalkyl group of four or five carbon atoms. The term "lower haloalkylthio," as used herein, refers to a lower alkylthio group substituted with one to three atoms of bromine, chlorine or fluorine. The term "lower alkenyl," as used herein, refers to a lower alkenyl group of two to four carbon atoms. The term "lower alkynyl," as used herein, refers to a lower alkynyl group of two to four carbon atoms.

The compounds of formula A are useful biological agents against plant pathogens. More particularly, the compounds of the present invention are useful fungicides and bacteriocides for the control of pathogenic diseases of plants. For example, during periods of adverse climactic conditions such as excess and prolonged moisture and mild to cool temperatures, many plants such as rice, tomato, peppers and cabbage and fruits are susceptible to and damaged by fungal and bacterial diseases caused by microorganisms belonging to Piricularia, Kanthomonas, Erwinia, and the like, such as the species *Piricularia oryzae*, *Xanthomonas oryzae* or *Erwinia amylovora*. The compounds of the present invention are useful in combating such diseases. The compounds of the present invention can generally be used either systemically or topically by conventional application methods. The compounds of the present invention are solids which may be formulated in suitable solid or liquid carriers in a conventional way for plant fungicidal or bacteriocidal formulations. The compounds of the present invention are usually applied at a concentration of from about 0.01 to 10.0 percent, by weight, or higher.

Suitable solid carriers include talc, kaolin, silica, and diatomaceous earth to which may be added wetting agents, dispersing agents, and the like, to form wettable powders. The wettable powder can be diluted with water to the desired concentration and applied to the soil and/or plant surface.

The compositions of the present invention, including compounds of formula A, display, variously, activity against the following diseases:

Bacterial diseases of plants such as *Xanthomonas campestris* on cabbage, *Xanthomonas vesicatoria* on peppers and *Xanthomonas malvacearus* on cotton.

Fungal diseases of other plants such as *Erysiphe graminis* on wheat and barley and other powdery mildews on various hosts such as *Sphaerotheca fuliginea* (cucurbits, e.g. cucumber), *Podosphaera leucotricha* (apples) and *Uncinula necator*.

*Puccinia recondita*, *Puccinia struformis* and other rusts on wheat; *Puccinia hordei*, *Puccinia struformis* and other rusts on barley; and rusts on other hosts, e.g. coffee, apples, vegetables and ornamental plants.

The compounds are also active against other diseases such as *Botrytis cinerea* (grey mould) on tomatoes, strawberries, vines and other hosts, and *Colletotrichum coffeanum* (berry disease) of coffee.

They can be used as industrial (as opposed to agricultural) bactericides and fungicides, e.g. as paint film fungicides. The compounds also have plant growth regulating properties.

The active ingredients may be used as such, for example for fungicidal or bactericidal purposes, but are more conveniently formulated into compositions for such usage.

The active ingredients of the invention compositions, and salts thereof, can be applied in a number of ways, for example they can be applied, formulated or unformulated, directly to the foliage of a plant, or they can be applied to bushes and trees, to seeds or to other medium in which plants, bushes or trees are growing or are to be planted, or they can be sprayed on, dusted on or applied as a cream or paste formulation, or they can be applied as a vapor. Application can be to any part of the plant, bush or tree, for example to the foliage, stems, branches or roots, or to soil or paddy water surrounding the roots, or to the seed before it is planted.

The term "plant" as used herein includes seedlings, bushes and trees. Furthermore, the fungicidal method of the invention includes preventative, protectant, prophylactic and eradicant treatment.

In a further aspect, therefore, the present invention provides a method for combating plant pests, especially fungi and bacteria, which comprises treating plants or seeds, or their loci, with a composition according to the invention and as herein defined.

In a further aspect the invention provides a method for combating the diseases *Xanthomonas oryzae* and *Pyricularia oryzae*, which comprises treating rice plants or seeds, or their locus, with a compound of formula A or a composition containing a compound of formula A.

The compositions may be in the form of dusting powders or granules comprising the active ingredient and a solid diluent or carrier, for example kaolin, bentonite, kieselguhr, dolomite, calcium carbonate, talc, powdered magnesia, Fuller's earth, gypsum, Hewitt's earth, diatomaceous earth and China clay. Compositions for dressing seed, for example, may comprise an agent (for example, a mineral oil) for assisting the adhesion of the composition to the seed. Alternatively, the active ingredient can be formulated for seed dressing purposes using an organic solvent (for example, N-methylpyrrolidone or dimethylformamide).

The compositions may also be in the form of dispersible powders, granules or grains comprising a wetting agent to facilitate their dispersion in liquids. The powders, granules or grains may also contain fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g., 2-ethoxyethanol and 2-butoxyethanol).

The compositions to be used as sprays may also be in the form of aerosols wherein the formulation is held in a container under pressure in the presence of a propellant, e.g., fluorotrichloromethane or dichlorodifluoromethane.

The active ingredients can be mixed in the dry state with a pyrotechnic mixture to form a composition suitable for generating in enclosed spaces a smoke containing the compounds.

Alternatively, the active ingredients may be used in a microencapsulated form.

By including suitable additives, for example additives for improving the distribution, adhesive power and resistance to rain on treated surfaces, the different compositions can be better adapted for various utilities.

The active ingredients can be used as mixtures with fertilizers (e.g., nitrogen-, potassium- or phosphorus-containing fertilizers). Compositions comprising only granules of fertilizer incorporating, for example coated with, a compound of formula A are preferred. Such granules suitably contain up to 25% by weight of the compound.

The invention therefore also provides, in a further aspect, a fertilizer composition comprising a compound of general formula A.

The compositions may also be in the form of liquid preparations for use as dips or sprays which are generally aqueous dispersions or emulsions containing the active ingredient in the presence of one or more wetting agent(s), dispersing agent(s), emulsifying agent(s) or suspending agent(s). These agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate; sodium, calcium or ammonium lignosulphonate; butyl-naphthalene sulphonate; and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient(s). When diluted to form aqueous preparations, such preparations may contain varying amounts of the active ingredient(s) depending on the intended purpose, but an aqueous preparation containing 0.0005% or 0.01% to 10% by weight of active ingredient(s) may be used.

The compositions can comprise also other compound(s) having biological activity [e.g., other growth stimulating substances such as the gibberellins (e.g., $GA_3$, $GA_4$ or $GA_7$), the auxins (e.g., indoleacetic or indolebutyric acid), and the cytokinins (e.g., kinetin, diphenylurea, benzimidazole and benzyladenine), and other compounds having complementary fungicidal or insecticidal activity], as well as stabilizing agent(s), for example epoxides (e.g., epichlorhydrin).

The following examples are provided to illustrate the practice of the present invention. Temperature is given in degrees centigrade.

EXAMPLE 1

A mixture of N-ethoxycarbonylcyanoacetamide (42 g), triethylorthoformate (40 g) and acetic anhydride (100 ml) is heated at reflux for one hour. The reaction is allowed to stand until cool and then is filtered, washing with ether, to yield α-cyano-β-ethoxy-N-ethoxycarbonylacrylamide.

To α-cyano-β-ethoxy-N-ethoxycarbonylacrylamide (1.2 g), dissolved in about 5 ml of boiling ethanol, is added 0.6 g of 2,6-dimethylaniline. The reaction is refluxed for several hours and then hexane is added. On cooling, the reaction is filtered, and washed with ethanol and ether to give α-cyano-β-(2,6-dimethylanilino)-N-ethoxycarbonylacrylamide, m.p. 138°–140°.

A mixture of α-cyano-β-(2,6-dimethylanilino)-N-ethoxycarbonylacrylamide (1.2 g) and about 10 ml of p-cymene is heated at reflux for about 1.5 hour. After cooling on standing, the crystalline product is collected by filtering and washing with ether to yield 5-cyano-1-(2,6-dimethylphenyl)uracil, m.p. 267°–269°.

Following the above procedure, each of 6-ethoxy-2-methylaniline, 6-chloro-2-methyl-4-methoxyaniline, 4-fluoro-2-methylaniline, 2,6-dimethyl-4-fluoroaniline, 3-chloro-2-methyl-6-methoxyaniline, 2-ethoxyaniline, 2-(1-propenyl)aniline and 2,6-dimethyl-4-methoxyaniline is reacted with α-cyano-β-ethoxy-N-ethoxycarbonylacrylamide and the product cyclized to give
b 5-cyano-1-(6-ethoxy-2-methylphenyl)uracil
5-cyano-1-(6-chloro-4-methoxy-2-methylphenyl)uracil
5-cyano-1-(4-fluoro-2-methylphenyl)uracil
5-cyano-1-(2,6-dimethyl-4-fluorophenyl)uracil
5-cyano-1-(3-chloro-6-methoxy-2-methylphenyl)uracil
5-cyano-1-(2-ethoxyphenyl)uracil
5-cyano-1-[2-(1-propenyl)phenyl]uracil
5-cyano-1-(2,6-dimethyl-4-methoxyphenyl)uracil.

EXAMPLE 2

To a warm solution of α-cyano-β-ethoxy-N-ethoxycarbonylacrylamide (14.8 g) and ethanol is added p-chloroaniline (8.9 g) in ethanol. Precipitate appears instantaneously. The mixture is stirred at room temperature for one hour and filtered to yield α-cyano-β-(4-chloroanilino)-N-ethoxycarbonylacrylamide, m.p. 177°–183°.

A mixture of 8.8 g (0.03 mol) of α-cyano-β-(4-chloroanilino)-N-ethoxycarbonylacrylamide and 40 ml of ortho-dichlorobenzene is heated at reflux. After about 2 hours, crystals appear and the mixture is allowed to cool to room temperature. The mixture is filtered to yield 5-cyano-1-(4-chlorophenyl)uracil, m.p. 236°–239°.

EXAMPLE 3

To 10.0 g of α-cyano-β-ethoxy-N-ethoxycarbonylacrylamide dissolved in about 40 ml of hot ethanol is added 6.45 g of 2,6-difluoroaniline in 15 ml of ethanol. The reaction mixture is stirred at reflux for about 6 hours, cooled and filtered to yield α-cyano-β-(2,6-difluoroanilino)-N-ethoxycarbonylacrylamide, white solid (12.61 g), which is added to 60 ml of tetralin and heated at reflux for 5 hours. The mixture is allowed to cool, filtered and washed with ether to yield 10.21 g of 5-cyano-1-(2,6-difluorophenyl)uracil, white solid.

EXAMPLE 4

A mixture of α-cyano-β-ethoxy-N-ethoxycarbonylacrylamide (10 g) and 45 ml of ethanol is heated to effect dissolution. Then 8.12 g of p-trifluoromethylaniline in 10 ml of ethanol is added and the mixture heated at reflux for 45 minutes. The mixture is cooled and filtered to give 14.01 g of α-cyano-β-(4-trifluoromethylanilino)-N-ethoxycarbonylacrylamide, which is added to about 60 ml of tetralin and heated at reflux for several hours. On formation of precipitate, the mixture is allowed to cool and then filtered, washed with ether, to yield 5-cyano-1-(4-trifluoromethylphenyl)uracil, m.p. 230.5°–231.5°.

Following the above procedure, p-methoxyaniline (0.05 mol) is reacted with α-cyano-β-ethoxy-N-ethoxycarbonyl-acrylamide (0.05 mol) to yield α-cyano-β-(4-methoxyanilino)-N-ethoxycarbonylacrylamide, which is cyclized by heating in tetralin to yield 5-cyano-1-(4-methoxyphenyl)uracil, m.p. 304.5°–306.5°.

3-Fluoroaniline (0.05 mol) is reacted with α-cyano-β-ethoxy-N-ethoxycarbonylacrylamide (0.05 mol) to yield α-cyano-β-(3-fluoroanilino)-N-ethoxycarbonylacrylamide, m.p. 169.5°–171.0°, which is heated at reflux in tetralin to yield 5-cyano-1-(3-fluorophenyl)uracil, m.p. 245.5°–246.5°.

2,6-Dichloroaniline and α-cyano-β-ethoxy-N-ethoxycarbonylacrylamide in ethanol is refluxed 3 days and hexane added to prepare α-cyano-β-(2,6-dichloroanilino)-N-ethoxycarbonylacrylamide, which is cyclized by heating in tetralin to yield 5-cyano-1-(2,6-dichlorophenyl)uracil, m.p. 273°–274.5°.

2,4,6-Trichloroaniline (0.04 mol) is reacted with α-cyano-β-ethoxy-N-ethoxycarbonylacrylamide (0.04 mol) by heating at reflux in ethanol to yield α-cyano-β-(2,4,6-trichloroanilino)-N-ethoxycarbonylacrylamide, which is cyclized by heating at reflux in 1,2-dichlorobenzene to yield crude product which is chromatographed on silica eluting with chloroform/acetone (3/1) to 5-cyano-1-(2,4,6-trichlorophenyl)uracil, pale yellow crystals, m.p. 245°–247°.

A mixture of α-cyano-β-ethoxy-N-ethoxycarbonylacrylamide (0.047 mol), 3,4-dichloroaniline (8.15 g) and ethanol (70 ml) is heated to prepare α-cyano-β-(3,4-dichloroanilino)-N-ethoxycarbonylacrylamide, which is cyclized by heating overnight in tetralin to yield 5-cyano-1-(3,4-dichlorophenyl)uracil, m.p. 206.5°–207.5°.

In the same way, 5-cyano-1-(3,5-dichlorophenyl)uracil is prepared starting with 3,5-dichloroaniline in place of 3,4-dichloroaniline.

EXAMPLE 5

Following the procedures hereinabove, each of 2-methoxyaniline, 4-nitroaniline, 4-ethylaniline, 4-methoxy-2-methylaniline, 4-(N,N-dimethyl)aniline, 2-bromoaniline, 4-methylaniline, 4-isopropylaniline, 4-t-butylaniline, 4-acetylaniline, 2-fluoroaniline, 2-cyanoaniline, 4-methylthioaniline, 2-fluoro-4-methylaniline, 4-chloro-2-fluoroaniline, 4-fluoro-2-methylaniline, 4-trifluoromethylthioaniline, 2-chloro-4-cyanoaniline, 4-chloro-2,6-difluoroaniline, 4-chloro-2-cyanoaniline, 2,4-dimethoxyaniline, 2-chloro-6-methylaniline, 4-cyclopropylaniline, 2,6-dimethyl-4-t-butylaniline, 2,4,6-trimethylaniline, 4-chloro-2,6-dimethylaniline, 2-trifluoromethylaniline, 3,4-methylenedioxyaniline, 4-bromo-2-fluoroaniline, 2-fluoro-4-trifluoromethylaniline, 2-chloro-4-trifluoromethylaniline, and 2-methyl-4-trifluoromethylaniline is reacted with α-cyano-β-ethoxy-N-ethoxycarbonylacrylamide to yield the respective β-anilino compound under col I, which is then cyclized to yield the respective 5-cyano-1-substituted phenyl uracil under col. II.

I (1) α-cyano-β-(2-methoxyanilino)-N-ethoxycarbonylacrylamide (2) α-cyano-β-(4-nitroanilino)-N-ethoxycarbonylacrylamide (3) α-cyano-β-(4-ethylanilino)-N-ethoxycarbonylacrylamide (4) α-cyano-β-(4-methoxy-2-methylanilino)-N-ethoxycarbonylacrylamide (5) α-cyano-β-(4-(N,N-dimethyl)anilino)-N-ethoxycarbonylacrylamide (6) α-cyano-β-(2-bromoanilino)-N-ethoxycarbonylacrylamide (7) α-cyano-β-(4-methylanilino)-N-ethoxycarbonylacrylamide (8) α-cyano-β-(4-isopropylanilino)-N-ethoxycarbonylacrylamide (9) α-cyano-β-(4-t-butylanilino)-N-ethoxycarbonylacrylamide

(10) α-cyano-β-(4-acetylanilino)-N-ethoxycarbonylacrylamide

(11) α-cyano-β-(2-fluoroanilino)-N-ethoxycarbonylacrylamide

(12) α-cyano-β-(2-cyanoaniline)-N-ethoxycarbonylacrylamide

(13) α-cyano-β-(4-methylthioanilino)-N-ethoxycarbonylacrylamide

(14) α-cyano-β-(2-fluoro-4-methylanilino)-N-ethoxycarbonylacrylamide

(15) α-cyano-β-(4-chloro-2-fluoroanilino)-N-ethoxycarbonylacrylamide

(16) α-cyano-β-(4-fluoro-2-methylanilino)-N-ethoxycarbonylacrylamide

(17) α-cyano-β-(4-trifluoromethylthioanilino)-N-ethoxycarbonylacrylamide

(18) α-cyano-β-(2-chloro-4-cyanoanilino)-N-ethoxycarbonylacrylamide

(19) α-cyano-β-(4-chloro-2,6-difluoroanilino)-N-ethoxycarbonylacrylamide

(20) α-cyano-β-(4-chloro-2-cyanoanilino)-N-ethoxycarbonylacrylamide

(21) α-cyano-β-(2,4-dimethoxyanilino)-N-ethoxycarbonylacrylamide

(22) α-cyano-β-(2-chloro-6-methylanilino)-N-ethoxycarbonylacrylamide

(23) α-cyano-β-(4-cyclopropylanilino)N-ethoxycarbonylacrylamide

(24) α-cyano-β-(2,6-dimethyl-4-t-butylanilino)-N-ethoxycarbonylacrylamide

(25) α-cyano-β-(2,4,6-trimethylanilino)-N-ethoxycarbonylacrylamide
(26) α-cyano-β-(4-chloro-2,6-dimethylanilino)-N-ethoxycarbonylacrylamide
(27) α-cyano-β-(2-trifluoromethylanilino)-N-ethoxycarbonylacrylamide
(28) α-cyano-β-(3,4-methylenedioxyanilino)-N-ethoxycarbonylacrylamide
(29) α-cyano-β-(4-bromo-2-fluoroanilino)-N-ethoxycarbonylacrylamide
(30) α-cyano-β-(2-fluoro-4-trifluoromethylanilino)-N-ethoxycarbonylacrylamide
(31) α-cyano-β-(2-chloro-4-trifluoromethylanilino)-N-ethoxycarbonylacrylamide
(32) α-cyano-β-(2-methyl-4-trifluoromethylanilino)-N-ethoxycarbonylacrylamide

II (1) 5-cyano-1-(2-methoxyphenyl)uracil, m.p. 236°–238°
(2) 5-cyano-1-(4-nitrophenyl)uracil, m.p. 269°–272°
(3) 5-cyano-1-(4-ethylphenyl)uracil, m.p. 223°–225°
(4) 5-cyano-1-(4-methoxy-2-methylphenyl)uracil, m.p. 276°–278°
(5) 5-cyano-1-(4-(N,N-dimethyl)phenyl)uracil, m.p. 309°–310°
(6) 5-cyano-1-(2-bromophenyl)uracil
(7) 5-cyano-1-(2-methylphenyl)uracil
(8) 5-cyano-1-(4-isopropylphenyl)uracil
(9) 5-cyano-1-(4-t-butylphenyl)uracil
(10) 5-cyano-1-(4-acetylphenyl)uracil
(11) 5-cyano-1-(2-fluorophenyl)uracil, m.p. 275° (dec.)
(12) 5-cyano-1-(2-cyanophenyl)uracil, m.p. 269°–275°
(13) 5-cyano-1-(4-methylthiophenyl)uracil
(14) 5-cyano-1-(2-fluoro-4-methylphenyl)uracil
(15) 5-cyano-1-(4-chloro-2-fluorophenyl)uracil
(16) 5-cyano-1-(4-fluoro-2-methylphenyl)uracil
(17) 5-cyano-1-(4-trifluoromethylthiophenyl)uracil
(18) 5-cyano-1-(2-chloro-4-cyanophenyl)uracil
(19) 5-cyano-1-(4-chloro-2,6-difluorophenyl)uracil
(20) 5-cyano-1-(4-chloro-2-cyanophenyl)uracil
(21) 5-cyano-1-(2,4-dimethoxyphenyl)uracil, m.p. 285° (dec.)
(22) 5-cyano-1-(2-chloro-6-methylphenyl)uracil
(23) 5-cyano-1-(4-cyclopropylphenyl)uracil
(24) 5-cyano-1-(2,6-dimethyl-4-t-butylphenyl)uracil
(25) 5-cyano-1-(2,4,6-trimethylphenyl)uracil, m.p. 276°–277°
(26) 5-cyano-1-(4-chloro-2,6-dimethylphenyl)uracil
(27) 5-cyano-1-(2-trifluoromethylphenyl)uracil, m.p. 258°–259°
(28) 5-cyano-1-(3,4-methylenedioxyphenyl)uracil
(29) 5-cyano-1-(4-bromo-2-fluorophenyl)uracil
(30) 5-cyano-1-(2-fluoro-4-trifluoromethylphenyl)uracil
(31) 5-cyano-1-(2-chloro-4-trifluoromethylphenyl)uracil
(32) 5-cyano-1-(2-methyl-4-trifluoromethylphenyl)uracil

EXAMPLE 6

α-Cyano-β-ethoxy-N-ethoxycarbonylcrotonamide (0.05 mol) is reacted with 2,6-dimethylaniline (0.05 mol) in hot ethanol using the procedure of Example 1 to yield α-cyano-β-(2,6-dimethylanilino)-N-ethoxycarbonylcrotonamide, which is cyclized by heating in tetralin to yield 5-cyano-1-(2,6-dimethylphenyl)-6-methyluracil, m.p. 302°–303°.

EXAMPLE 7

To a mixture of 5-cyano-1-(2,6-dimethylphenyl)uracil (0.1 mol) and 80 ml of five percent sodium hydroxide solution, with stirring, is slowly added dimethyl sulfate (0.1 mol). The reaction mixture is stirred for about 2 hours and then filtered, washed with water and dried to yield 5-cyano-1-(2,6-dimethylphenyl)-3-methyluracil, m.p. 198.2°–199.5°.

Following the above procedure, 5-cyano-3,6-dimethyl-1-(2,6-dimethylphenyl)uracil is prepared from 5-cyano-1-(2,6-dimethylphenyl)-6-methyluracil.

EXAMPLE 8

Ten grams of α-cyano-β-ethoxy-N-ethoxycarbonylacrylamide in dissolved by heating in 50 ml of ethanol to 60°. Then 5.32 g of 2-methylaniline in 20 ml ethanol is added and the mixture heated at reflux for 4 hours with stirring. Crystals appear on cooling and the mixture is filtered and washed with ether to yield 11.36 g of α-cyano-β-(2-methylanilino)-N-ethoxycarbonylacrylamide, which is dissolved in tetralin and heated at reflux for 3 hours. After cooling, the mixture is filtered, washed with ether, to yield 5-cyano-1-(2-methylphenyl)uracil, m.p. 251.5°–252.5°.

The above process is repeated using 0.05 mol of 4-cyanoaniline in place of 2-methylaniline to yield 10.43 g of 5-cyano-1-(4-cyanophenyl)uracil, m.p. 324°–326° (dec.).

The above process is repeated using 6.83 g of 4-methoxy-2-methylaniline in place of 2-methylaniline to yield 5-cyano-1-(4-methoxy-2-methylphenyl)uracil, m.p. 276.5°–277.5°.

EXAMPLE 9

A mixture of 5-cyano-1-(2,6-dimethylphenyl)uracil (0.01 mol) and 30 ml of 48% HBr is heated at reflux for about 10 hours. After cooling, the solid product is collected by filtering, washed with water and dried to yield 1-(2,6-dimethylphenyl)uracil.

5-Cyano-3-methyl-1-(2,6-dimethylphenyl)uracil is hydrolyzed using the above procedure to prepare 1-(2,6-dimethylphenyl)-3-methyluracil.

EXAMPLE 10

A mixture of 5-cyano-1-(2,6-dimethylphenyl)uracil (0.01 mol) and 50 ml of 48% HBr is heated at reflux for about 2 hours. After cooling, the solid reaction product is collected by filtration, washed with water and dried to yield 5-carbamoyl-1-(2,6-dimethylphenyl)uracil, m.p. 315° (dec.).

EXAMPLE 11

A mixture of 5-cyano-1-(2,6-dimethylphenyl)uracil (0.01 mol) and 50 ml of NaOH (2.5 N) is heated for 2 hours at about 90°. After cooling, a small amount of dilute HCl is added to precipitate product. The mixture is filtered and the collected precipitate washed with water to yield 5-carbamoyl-1-(2,6-dimethylphenyl)uracil.

EXAMPLE 12

A solution of α-cyano-β-ethoxy-N-ethoxycarbonylacrylamide (0.05 mol) and 2,6-dimethylaniline (0.05 mol) in 75 ml ethanol is refluxed for several hours until the 2,6-dimethylaniline disappears as checked by thin layer chromatography. On cooling, (precipitate not formed) hexane (about 400 ml) is added and the mixture is filtered to yield 10.52 g of α-cyano-β-(2,6-dimethylanilino)-N-ethoxycarbonylacrylamide, m.p. 138°-140°, which is cyclized by heating in ortho-dichlorobenzene for about 4 hours to yield 5-cyano-1-(2,6-dimethylphenyl)uracil.

EXAMPLE 13

Following the procedures hereinabove, each of the anilines under col. III is reacted with α-cyano-β-ethoxy-N-ethoxycarbonylacrylamide to yield the respective β-anilino compound, which is then cyclized to yield the respective 5-cyano-1-substituted phenyl uracil under col. IV.

III 2-chloro-4-methylaniline
4-chloro-2-methylaniline
2-chloroaniline
3,5-dimethoxyaniline
6-chloro-2-methylaniline
3-acetylaniline
4-chloro-3-trifluoromethylaniline
2-chloro-5-nitroaniline
3-chloro-4-fluoroaniline
2,3-dichloroaniline
5-methyl-2-nitroaniline
2-methylthioaniline
3,4-dimethoxyaniline
4-n-butylaniline
3-chloroaniline
2-chloro-5-trifluoromethylaniline
3-chloro-2-methylaniline
2-isopropylaniline
3-methylaniline
3-trifluoromethylaniline
4-hydroxy-2-methylaniline
4-fluoroaniline
2,4-difluoroaniline

IV 5-cyano-1-(2-chloro-4-methylphenyl)uracil, m.p. 249°-250°
5-cyano-1-(4-chloro-2-methylphenyl)uracil, m.p. 230°-231°
5-cyano-1-(2-chlorophenyl)uracil, m.p. 260°-262°
5-cyano-1-(3,5-dimethoxyphenyl)uracil, m.p. 236°-238°
5-cyano-1-(6-chloro-2-methylphenyl)uracil, m.p. 241°-243°
5-cyano-1-(3-acetylphenyl)uracil, m.p. 270°-271°
5-cyano-1-(4-chloro-3-trifluoromethylphenyl)uracil, m.p. 231°-232°
5-cyano-1-(2-chloro-5-nitrophenyl)uracil, m.p. 244° (dec.)
5-cyano-1-(3-chloro-4-fluorophenyl)uracil, m.p. 193°-196°
5-cyano-1-(2,3-dichlorophenyl)uracil, m.p. 235°-240°
5-cyano-1-(5-methyl-2-nitrophenyl)uracil, m.p. 295°-300° (dec)
5-cyano-1-(2-methylthiophenyl)uracil, m.p. 215°-219°
5-cyano-1-(3,4-dimethoxyphenyl)uracil, m.p. 222°-225°
5-cyano-1-(4-n-butylphenyl)uracil, m.p. 181°-183°
5-cyano-1-(3-chlorophenyl)uracil, m.p. 228°-231°
5-cyano-1-(2-chloro-5-trifluoromethylphenyl)uracil, m.p. 170°-172°
5-cyano-1-(3-chloro-2-methylphenyl)uracil, m.p. 225°
5-cyano-1-(2-isopropylphenyl)uracil, m.p. 153°-156°
5-cyano-1-(3-methylphenyl)uracil, m.p. 235°-237°
5-cyano-1-(3-trifluoromethylphenyl)uracil, m.p. 155°-157°
5-cyano-1-(4-hydroxy-2-methylphenyl)uracil, m.p. 292°-294°
5-cyano-1-(4-fluorophenyl)uracil, m.p. 224°-226°
5-cyano-1-(2,4-difluorophenyl)uracil, m.p. 216°-219°

EXAMPLE 14

Following procedures hereinabove, each of aniline and 4-bromoaniline is reacted with α-cyano-β-ethoxy-N-ethoxycarbonylacrylamide and cyclized to yield 5-cyano-1-phenyluracil, m.p. 290°, and 5-cyano-1-(4-bromophenyl)uracil, m.p. 257°-260°. The foregoing two compounds have been reported by Atkinson et al., *J. Chem. Soc.* 4118-4123 (1956) and Senda et al., *Chem Pharm. Bull.* 22(1), 189-195 (1974), respectively.

EXAMPLE 15

Following procedures hereinabove, each of the anilino compounds under col. V is reacted with α-cyano-β-ethoxy-N-ethoxycarbonylacrylaminde and then cyclized to yield the respective uracil compound under col. VI.

V 2-methylthioaniline
2-trifluoromethoxyaniline
2-difluoromethoxyaniline
2-ethyl-6-methylaniline
2-methyl-6-trifluoromethylaniline
2,6-dimethoxyaniline
2-methyl-6-methylthioaniline
2-fluoro-6-methylaniline
2,3-dimethylaniline
3-fluoro-2-methylaniline
2-methyl-4-methylthioaniline
2,4-dimethylaniline
4-ethyl-2-methylaniline
3-methylaniline
3-methoxyaniline
2,3,5-trimethylaniline
3,5-dichloro-2-methylaniline
2,3,6-trimethylaniline
3,5-difluoro-2-methylaniline

VI 5-cyano-1-(2-methylthiophenyl)uracil
5-cyano-1-(2-trifluoromethoxyphenyl)uracil
5-cyano-1-(2-difluoromethoxyphenyl)uracil
5-cyano-1-(2-ethyl-6-methylphenyl)uracil
5-cyano-1-(2-methyl-6-trifluoromethylphenyl)uracil
5-cyano-1-(2,6-dimethoxyphenyl)uracil
5-cyano-1-(2-methyl-6-methylthiophenyl)uracil
5-cyano-1-(2-fluoro-6-methylphenyl)uracil
5-cyano-1-(2,3-dimethylphenyl)uracil
5-cyano-1-(3-fluoro-2-methyl)uracil
5-cyano-1-(2-methyl-4-methylthiophenyl)uracil
5-cyano-1-(2,4-dimethylphenyl)uracil
5-cyano-1-(4-ethyl-2-methylphenyl)uracil
5-cyano-1-(3-methylphenyl)uracil
5-cyano-1-(3-methoxyphenyl)uracil
5-cyano-1-(2,3,5-trimethylphenyl)uracil
5-cyano-1-(3,5-dichloro-2-methylphenyl)uracil
5-cyano-1-(2,3,6-trimethylphenyl)uracil
5-cyano-1-(3,5-difluoro-2-methylphenyl)uracil

EXAMPLE 16

An emulsifiable concentrate was made up by mixing the ingredients, and stirring the mixture until all the constituents were dissolved.

| | |
|---|---|
| Compound of Example 1 | 10% |
| Ethylene dichloride | 40% |
| Calcium dodecylbenzenesulphate | 5% |
| "Lubrol" L | 10% |
| "Aromasol" H | 35% |

EXAMPLE 17

A composition in the form of grans readily dispersible in a liquid, e.g. water, was prepared by grinding together the first three ingredients in the presence of added water and then mixing in the sodium acetate. The resultant mixture was dried and passed through a British Standard mesh sieve, size 44-100, to obtain the desired size of grains.

| | |
|---|---|
| Compound of Example 1 | 50% |
| "Dipersol" T | 25% |
| "Lubrol" APN 5 | 1.5% |
| Sodium acetate | 23.5% |

EXAMPLE 18

The ingredients were all ground together to produce a powder formulation readily dispersible in liquids.

| | |
|---|---|
| Compound of Example 5 (#4) | 45% |
| "Dispersol" T | 5% |
| "Lissapol" NX | 0.5% |
| "Cellofas" B600 | 2% |
| Sodium acetate | 47.5% |

EXAMPLE 19

The active ingredient was dissolved in a solvent and the resultant liquid was sprayed onto the granules of China clay. The solvent was then allowed to evaporate to produce a granular composition.;

| | |
|---|---|
| Compound of Example 8 (first made) | 5% |
| China clay granules | 95% |

EXAMPLE 20

A composition suitable for use as a seed dressing was prepared by mixing the three ingredients.

| | |
|---|---|
| Compound of Example 8 (last made) | 50% |
| Mineral oil | 2% |
| China clay | 48% |

EXAMPLE 21

A dusting powder was prepared by mixing the active ingredient with talc.

| | |
|---|---|
| Compound of Example 5 (#1) | 5% |
| Talc | 95% |

EXAMPLE 22

A Col formulation was prepared by ball-milling the constituents set out below and then forming an aqueous suspension of the ground mixture with water.

| | |
|---|---|
| Compound of Example 15 (first made) | 40% |
| "Dispersol" T | 10% |
| "Lubrol" APN 5 | 1% |
| Water | 49% |

EXAMPLE 23

A dispersible powder formulation was made by mixing together the ingredients set out below and then grinding the mixture until all were thoroughly mixed.

| | |
|---|---|
| Compound of Example 5 (#16) | 25% |
| "Aerosol" OT/B | 2% |
| "Dispersol" A.C. | 5% |
| China clay | 28% |
| Silica | 40% |

EXAMPLE 24

This Example illustrates the preparation of a dispersible powder formulation. The ingredients were mixed and the mixture then ground in a comminution mill.

| | |
|---|---|
| Compound of Example 5 (#1) | 25% |
| "PERMINAL" BX | 1% |
| "Dispersol" T | 5% |
| Polyvinylpyrrolidone | 10% |
| Silica | 25% |
| China clay | 34% |

EXAMPLE 25

The ingredients set out below were formulated into a dispersible powder by mixing and then grinding the ingredients.

| | |
|---|---|
| Compound of Example 1 | 25% |
| "Aerosol" OT/B | 2% |
| "Dispersol" A | 5% |
| China clay | 68% |

In Examples 16 to 25 the proportions of the ingredients given are by weight.

The substances represented by the various trademarks and tradenames are as follows:

LUBROL L: A condensate of nonyl phenol (1 mole) with ethylene oxide (13 moles).

AROMASOL H: A solvent mixture of alkylbenzenes.

DISPERSOL T AND AC: A mixture of sodium sulphate and a condensate of formaldehyde with sodium naphthalene sulphonate.

LUBROL APN 5: A condensate of nonyl phenol (1 mole) with naphthalene oxide (5.5 moles).

CELLOFAS B600: A sodium carboxymethyl cellulose thickener.

LISSAPOL NX: A condensate of nonyl phenol (1 mole) with ethylene oxide (8 moles).

AEROSOL OT/B: Dioctyl sodium sulphosuccinate.

PERMINAL BX: A sodium alkyl naphthalene sulphonate.

EXAMPLE 26

The active ingredients (test compounds) were tested against a variety of foliar fungal diseases of plants. The technique employed was as follows:

The plants were grown in John Innes Potting Compost (No. 1, or Seed, as appropriate) in 4 cm diameter mini-pots. A layer of fine sand was placed at the bottom of the pot to facilitate uptake of test compound by the roots. Vermiculite was used to cover the seed in the soil tests.

The test compounds were formulated either by bead-milling with aqueous Dispersol T or as a solution in acetone/ethanol which was diluted to the required concentration immediately before use. For the foliage diseases, 100 ppm A.I. suspensions were sprayed onto the foliage and applied to the roots of the same plant via the soil. (Sprays were applied to maximum retention, and root drenches to a final concentration equivalent to approximately 40 ppm A.I./dry soil). Tween 20, to give a final concentration of 0.05%, was added when the sprays were applied to the cereals and rusts.

For most of the tests, the test compound was applied to the soil (roots) and to the foliage (by spraying) one or two days before the plant was inoculated with the disease. After inoculation, the plants were put into an appropriate environment to allow infection to take place and then incubated until the disease was ready for assessment.

The period between inoculation and assessment varied from 4 to 14 days according to the disease and environment.

The disease control was recorded by the following grading:
4 = No disease
3 = 0–5%
2 = 6–25%
1 = 26–60%
0 = >60%

The results are shown in Table I.

TABLE I

| COMPOUND NO. | PYRICULARIA ORYZAE (rice) |
|---|---|
| Example No. 1 | 4 |
| Example No. 5 | 4 |
| (first compound) | |
| Example No. 8 | 4 |
| (first compound) | |
| Example No. 15 | 3 |
| (first compound) | |

EXAMPLE 27

This Example illustrates the control of the rice bacterial disease *Xanthomonas oryzae* according to the invention process. The test procedure is described below and thereafter, in Table II, are set out the results.

Rice seedlings at the one to two leaf stage were root drenched (10 ml) and sprayed with the chemical compound under test. Forty-eight hours later, the plants were inoculated by cutting off the tips of the leaves with scissors dipped in a dispersion of a billion cells/ml ($10^9$ cells/ml) of *Xanthomonas oryzae*. After 7 days at 100% relative humidity at 30° C., the seedlings were assessed for diasease on a 0-4 scale, where 0 is no control, 1 is slight control, 2 is fair control, 3 is good control and 4 is complete control. Results are shown in Table II below.

TABLE II

| Compound | Rate of Application in Parts per Million (ppm) | Root Drench Test | Spray Test |
|---|---|---|---|
| Example No. 1 | 50 | 4 | 4 |
|  | 10 | 4 | 3 |
| Example No. 8 | 50 | 4 | 4 |
| (first compound) | 10 | 4 | 2 |
| Example No. 15 | 50 | 4 | 0 |
| (first compound) | 10 | 3 | 0 |
| Example No. 5 | 50 | 4 | 4 |
| (first compound) | 10 | 4 | 0 |

What is claimed is:

1. A compound of the following formula (III):

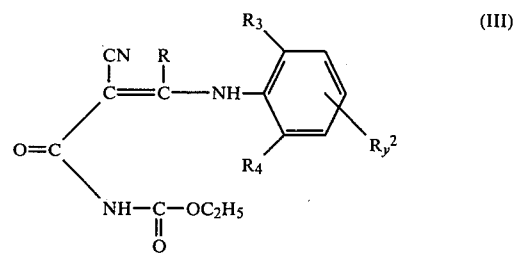

wherein,

R is hydrogen, methyl or ethyl;

$R^2$ is lower alkyl, lower alkoxy, bromo, chloro, fluoro, lower haloalkyl, cyano, nitro, lower alkylthio, hydroxy, lower alkylcarbonyl, lower alkoxycarbonyl, lower haloalkoxy, cycloalkyl, clycloalkalkyl, lower haloalkylthio, lower alkenyl or lower alkynyl;

$R^3$ is hydrogen or independently selected from the values of $R^2$;

$R^4$ is hydrogen or independently selected from the values of $R^2$; and y is zero, one, two or three, provided that:

(a) when R is hydrogen, $R^2$ is bromo, and y is one—then either $R^3$ or $R^4$ is other than hydrogen and (b) when R is hydrogen—then either $R^3$ or $R^4$ is other than hydrogen or y is one, two or three.

2. A compound according to claim 1 wherein y is zero, each of $R^3$ and $R^4$ is methyl and R is hydrogen.

3. A compound according to claim 1 wherein y is zero and each of R, $R^3$ and $R^4$ is methyl.

4. A compound according to claim 1 wherein R is hydrogen.

5. A compound according to claim 1 wherein each of R and $R^4$ is hydrogen and y is zero.

6. A compound according to claim 5 wherein $R^3$ is lower alkyl of 1 to 4 carbon atoms, lower alkoxy of 1 to 4 carbon atoms, chloro, fluoro, fluoroalkyl of 1 or 2 carbon atoms, lower alkythio of 1 or 2 carbon atoms, lower alkylcarbonyl of 2 to 4 carbon atoms or fluoroalkoxy of 1 or 2 carbon atoms.

7. A compound according to claim 5 wherein $R^3$ is methyl, ethyl, methoxy, ethoxy, trifluoromethyl, methylthio, ethylthio, acetyl, trifluoromethoxy or difluoromethoxy.

8. A compound according to claim 4 wherein y is zero and each of $R^3$ and $R^4$ is independently selected from lower alkyl of 1 to 4 carbon atoms, lower alkoxy of 1 to 4 carbon atoms, chloro, fluoro, fluoroalkyl of 1 or 2 carbon atoms, lower alkylthio of 1 or 2 carbon atoms, lower alkycarbonyl of 2 to 4 carbon atoms and fluoroalkoxy of 1 or 2 carbon atoms.

9. A compound according to claim 4 hwerein y is zero and each of $R^3$ and $R^4$ is independently selected from methyl, ethyl, methoxy, chloro, fluoro, trifluoromethyl, methylthio, acetyl and trifluoromethoxy.

10. A compound according to claim 4 wherein $R^4$ is hydrogen; each of $R^2$ and $R^3$ is independently selected from lower alkyl of 1 to 4 carbon atoms, lower alkoxy of 1 to 4 carbon atoms, chloro, fluoro, fluoroalkyl of 1 or 2 carbon atoms, lower alkylthio of 1 or 2 carbon atoms, lower alkycarbonyl of 2 to 4 carbon atoms and fluoroalkoxy of 1 or 2 carbon atoms; and y is one or two.

11. A compound according to claim 4 wherein $R^4$ is hydrogen; $R^3$ is methyl, ethyl, methoxy, methylthio or trifluoromethyl; and $R^2$ is methyl, ethyl, methoxy, methylthio, trifluoromethyl, fluoro or chloro.

12. A compound according to claim 11 wherein $R^2$ is methyl, ethyl or methoxy and y is one.

13. A compound according to claim 12 wherein $R^2$ is in the 3 position.

14. A compound according to claim 12 wherein $R^2$ is chloro or fluoro in the 3 position and $R^3$ is methyl.

15. A compound according to claim 12 wherein $R^2$ is in the 4 position.

16. A compound according to claim 15 wherein $R^2$ is methoxy in the 4 position and $R^3$ is methyl.

17. A compound according to claim 4 wherein each of $R^3$ and $R^4$ is hydrogen and $R^2$ is fluoro, methyl or methoxy.

18. A compound according to claim 17 wherein $R^2$ is fluoro in the 4 position and y is one.

19. A compound according to claim 17 wherein $R^2$ is methyl or methoxy in the 3 position and y is one.

* * * * *